US007919332B2

(12) United States Patent
Haruyama

(10) Patent No.: US 7,919,332 B2
(45) Date of Patent: Apr. 5, 2011

(54) BIOLOGICAL MOLECULE-IMMOBILIZED CHIP AND ITS USE

(75) Inventor: Tetsuya Haruyama, Kitakyushu (JP)

(73) Assignee: Kitakyushu Foundation for the Advancement of Industry Science and Technology, Kitakyushu-shi, Fukuoka (JP)

( * ) Notice: Subject to any disclaimer, the term of this patent is extended or adjusted under 35 U.S.C. 154(b) by 747 days.

(21) Appl. No.: 10/548,945

(22) PCT Filed: Feb. 27, 2004

(86) PCT No.: PCT/JP2004/002410
§ 371 (c)(1),
(2), (4) Date: Sep. 14, 2005

(87) PCT Pub. No.: WO2004/081567
PCT Pub. Date: Sep. 23, 2004

(65) Prior Publication Data
US 2008/0096219 A1     Apr. 24, 2008

(30) Foreign Application Priority Data

Mar. 14, 2003  (JP) .................................. 2003-069924
Aug. 11, 2003  (JP) .................................. 2003-207081

(51) Int. Cl.
*G01N 33/553*     (2006.01)
(52) U.S. Cl. ..... 436/525; 436/518; 436/524; 435/283.1; 435/287.1; 435/287.2; 435/288.3; 435/288.7
(58) Field of Classification Search ............... 435/283.1, 435/287.1, 287.2, 288.3, 288.7; 436/518, 436/524, 525
See application file for complete search history.

(56) References Cited

U.S. PATENT DOCUMENTS

| 5,439,829 | A | * | 8/1995 | Anderson et al. ............. 436/518 |
| 5,958,701 | A | * | 9/1999 | Green et al. ...................... 435/6 |
| 6,365,378 | B1 | | 4/2002 | Hirota et al. |
| 7,690,324 | B1 | * | 4/2010 | Feng et al. ...................... 118/52 |
| 2001/0005322 | A1 | | 6/2001 | Uchida |
| 2001/0053522 | A1 | | 12/2001 | Makino et al. |
| 2002/0102617 | A1 | | 8/2002 | MacBeath et al. |
| 2002/0123043 | A1 | | 9/2002 | Hutchens et al. |
| 2003/0003223 | A1 | | 1/2003 | Morse et al. |
| 2003/0013130 | A1 | | 1/2003 | Charych et al. |
| 2003/0023037 | A1 | * | 1/2003 | Tchaga ......................... 530/350 |
| 2004/0171077 | A1 | * | 9/2004 | Lubenow et al. .............. 435/7.1 |
| 2004/0209269 | A1 | * | 10/2004 | Dugas et al. ...................... 435/6 |
| 2005/0053964 | A1 | * | 3/2005 | Bamdad et al. ................... 435/6 |

FOREIGN PATENT DOCUMENTS

| EP | 0 339 821 | 11/1989 |
| JP | 2001-083155 | 3/2001 |
| JP | 2001-343386 | 12/2001 |
| JP | 2002-017352 A | 1/2002 |
| WO | WO 02/01228 | 1/2002 |

OTHER PUBLICATIONS

Hochuli, et al. "Genetic Approach to Facilitate Purification of Recombinant Proteins with a Novel Metal Chelate Adsorbent," *Bio/Technology*, vol. 6, No. 11, pp. 1321-1325, Nov. 1, 1988.

* cited by examiner

*Primary Examiner* — Melanie J Yu
(74) *Attorney, Agent, or Firm* — Knobbe, Martens, Olson & Bear, LLP

(57) ABSTRACT

A biological molecule-immobilized chip is produced by: allowing a biological molecule having a portion capable of forming coordination bond to a metal ion to form a coordination bond to a metal ion, bringing the resultant complex adjacent to an electrically conductive support, and applying reduction potential to the electrically conductive support.

10 Claims, 4 Drawing Sheets

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial
<220> FEATURE:
<223> OTHER INFORMATION: primer

<400> SEQUENCE: 1
gctgcagtag acaacaaatt caacaaagaa c                              31

<210> SEQ ID NO 2
<211> LENGTH: 31
<212> TYPE: DNA
<213> ORGANISM: Artificial
<220> FEATURE:
<223> OTHER INFORMATION: primer

<400> SEQUENCE: 2
cggtaccgtc tacttttggt gcttgagcat c                              31

<210> SEQ ID NO 3
<211> LENGTH: 177
<212> TYPE: DNA
<213> ORGANISM: Staphylococcus aureus
<220> FEATURE:
<221> NAME/KEY: CDS
<222> LOCATION: (1)..(177)
<223> OTHER INFORMATION:

<400> SEQUENCE: 3 gac aac aaa ttc aac aaa gaa caa caa aat gct ttc tat gaa att tta        48
Asp Asn Lys Phe Asn Lys Glu Gln Gln Asn Ala Phe Tyr Glu Ile Leu
1               5                   10                  15 cat tta cct aac tta act gaa gaa caa cgt aac ggc ttc atc caa agc        96
His Leu Pro Asn Leu Thr Glu Glu Gln Arg Asn Gly Phe Ile Gln Ser
            20                  25                  30 ctt aaa gac gat cct tca gtg agc aaa gaa att tta gca gaa gct aaa       144
```

```
Leu Lys Asp Asp Pro Ser Val Ser Lys Glu Ile Leu Ala Glu Ala Lys
        35                  40                  45 aag cta aac gat gct caa gca cca aaa gct aga                         177
Lys Leu Asn Asp Ala Gln Ala Pro Lys Ala Arg
    50                  55

<210> SEQ ID NO 4
<211> LENGTH: 59
<212> TYPE: PRT
<213> ORGANISM: Staphylococcus aureus

<400> SEQUENCE: 4

Asp Asn Lys Phe Asn Lys Glu Gln Gln Asn Ala Phe Tyr Glu Ile Leu
1               5                   10                  15

His Leu Pro Asn Leu Thr Glu Glu Gln Arg Asn Gly Phe Ile Gln Ser
            20                  25                  30

Leu Lys Asp Asp Pro Ser Val Ser Lys Glu Ile Leu Ala Glu Ala Lys
        35                  40                  45

Lys Leu Asn Asp Ala Gln Ala Pro Lys Ala Arg
    50                  55

<210> SEQ ID NO 5
<211> LENGTH: 177
<212> TYPE: DNA
<213> ORGANISM: Artificial
<220> FEATURE:
<223> OTHER INFORMATION: complementary

<400> SEQUENCE: 5
tctagctttt ggtgcttgag catcgtttag cttttttagct tctgctaaaa tttctttgct    60
cactgaagga tcgtctttaa ggctttggat gaagccgtta cgttgttctt cagttaagtt   120
aggtaaatgt aaaatttcat agaaagcatt tgttgttct ttgttgaatt tgttgtc       177

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ccatcatcac caccatcact a                                               21

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
agcttagtga tggtggtgat gatgggtac                                       29

<210> SEQ ID NO 8
<211> LENGTH: 8
<212> TYPE: PRT
<213> ORGANISM: Artificial
<220> FEATURE:
<223> OTHER INFORMATION: poly Histidine

<400> SEQUENCE: 8

Gly Thr His His His His His His
1               5
```

US 7,919,332 B2

BIOLOGICAL MOLECULE-IMMOBILIZED CHIP AND ITS USE

RELATED APPLICATIONS

This is the U.S. National Phase under 35 U.S.C. §371 of International Application PCT/JP2004/002410, filed Feb. 27, 2004, which was published in a language other than English which claims priority of Japanese Patent Application No. 2003-207081, filed Aug. 11, 2003 and Japanese Patent Application No. 2003-069924, filed Mar. 14, 2003.

TECHNICAL FIELD

The present invention relates to a biological molecule-immobilized chip, a method of manufacturing the same, and its use. Specifically, the present invention relates to a biological molecule-immobilized chip comprising an electrically conductive support and a biological molecule such as a protein immobilized on the support via a metallic atom.

BACKGROUND ART

Protein chip is useful for analysis of a protein-binding molecule and the like. To attain such objects, protein should be stably immobilized in the same orientation. An entrapment method (Journal of Electroanalytical Chemistry, vol. 347, pp 293-301 (1993)) and a polymerization method (Journal of Electroanalytical Chemistry, vol. 511, pp 128-133 (2001)) have been known as typical immobilizing techniques for proteins. However, either of those methods has a problem in that the orientation of immobilized proteins cannot be controlled. Self-accumulation method (Sensors and Actuator B, vol. 24-25, pp 113-116 (1995)) is also known that utilizes mercapto-bond of a sulfur atom of cysteine to the surface of a metal such as gold having high crystallinity. However, the self-accumulation method has problems such as a decrease of activity of a protein and disarray of orientation because cysteine residues exist in many parts of the protein structure and reaction proceeds in each of the cysteine residues. In addition, the immobilization methods as described above are irreversible, which does not allow immobilized proteins to re-dissociate, so that it is difficult to reuse substrates and proteins, and also difficult to analyze a small amount of samples bound to the immobilized proteins.

Another technique in which proteins are bound to metal ions by using a metal-binding polypeptide such as polyhistidine fused to a protein in order to control the orientation of immobilized proteins is also known (JP 2001-083155 A). However, a bond between the metal-binding polypeptide and the metal ion is apt to dissociate because of a competitive reaction of coordination bond, and therefore the method is not suitable for stable immobilization.

DISCLOSURE OF THE INVENTION

An object of the present invention is to provide a biological molecule-immobilized chip in which a biological molecule such as a protein is stably immobilized on an electrically conductive support in a constant orientation. Another object of the present invention is to provide an analysis method using the biological molecule-immobilized chip; and a purification method of a biological molecule.

The inventor of the present invention found that a protein can be stably immobilized on an electrically conductive support by allowing a protein having a portion capable of forming a coordination bond to a metal ion to form a coordination bond to a metal ion; bringing the resultant complex adjacent to the electrically conductive support; and applying a reduction potential to the electrically conductive support. The inventor of the present invention also found that a protein chip in which the protein is immobilized stably on the electrically conductive support in a constant orientation can be prepared by means of the immobilizing technique. Furthermore, the inventor of the present invention found that the protein can be re-dissociated by applying an oxidation potential to the electrically conductive support on which the protein is immobilized. Based on these findings, the inventor completed the present invention.

That is, the present invention is the followings.

(1) A biological molecule-immobilized chip, wherein said chip comprises an electrically conductive support and biological molecule immobilized on the electrically conductive support via a metallic atom, and wherein said biological molecule has a portion capable of forming a coordination bond to a metal ion, and said metallic atom is generated by reduction of the metal ion.

(2) The biological molecule-immobilized chip according to (1), wherein said electrically conductive support has a pointed top, and said biological molecule is immobilized on the pointed top of the electrically conductive support via a metallic atom.

(3) The biological molecule-immobilized chip according to (1) or (2), wherein said electrically conductive support is carried on a substrate.

(4) The biological molecule-immobilized chip according to any one of (1) to (3), wherein said portion capable of forming a coordination bond to a metal ion is polyhistidine.

(5) The biological molecule-immobilized chip according to any one of (1) to (4), wherein said electrically conductive support is a metal.

(6) The biological molecule-immobilized chip according to any one of (1) to (4), wherein said electrically conductive support is one or more metals selected from the group consisting of gold, silver, copper, aluminum, and platinum.

(7) The biological molecule-immobilized chip according to any one of (1) to (6), wherein said metallic atom is a metallic atom generated by reduction of a divalent metal ion.

(8) The biological molecule-immobilized chip according to any one of (1) to (7), wherein said biological molecule is a protein.

(9) A method of manufacturing a biological molecule-immobilized chip, which comprises the steps of:

allowing a biological molecule having a portion capable of forming coordination bond to a metal ion to form coordination bond to a metal ion;

bringing the resultant complex adjacent to an electrically conductive support; and applying a reduction potential to the electrically conductive support, and thereby immobilizing the biological molecule having the portion capable of forming coordination bond to a metal ion on the electrically conductive support.

(10) A method of analyzing a biological molecule or a molecule in a sample, comprising:

reacting a biological molecule immobilized on the biological molecule-immobilized chip according to any one of (1) to (8) with a sample containing a molecule capable of specifically binding to the biological molecule;

detecting a molecule bound indirectly to the chip via binding to the immobilized biological molecule, and analyzing the biological molecule immobilized on the biological molecule-immobilized chip or the molecule in a sample.

(11) A method of analyzing a biological molecule or a molecule in a sample, comprising:

reacting the biological molecule immobilized on the chip according to any one of (1) to (8) with a sample containing a molecule capable of specifically binding to the immobilized biological molecule; and dissociating a complex containing the immobilized biological molecule and the molecule specifically binding to the biological molecule obtained from the reaction, from an electrically conductive support of the chip by applying an oxidation potential to the electrically conductive support.

(12) A method of purifying a biological molecule comprising the steps of:

immersing an electrically conductive support in a solution containing a metal ion and a biological molecule having and a portion capable of forming a coordination bond to the metal ion;

applying a reduction potential to the electrically conductive support to immobilize the biological molecule on the electrically conductive support;

immersing the electrically conductive support obtained in the above step on which the biological molecule is immobilized, in a solution for dissociation; and applying an oxidation potential to the electrically conductive support to dissociate the biological molecule from the electrically conductive support.

(13) A method of immobilizing a molecule comprising the steps of:

allowing a molecule having a portion capable of forming a coordination bond to a metal ion to form a coordination bond to a metal ion;

brining the resultant complex adjacent to an electrically conductive support; and applying a reduction potential to the electrically conductive support to immobilize the molecule on the electrically conductive support.

(14) The method according to(13), wherein said molecule is a protein.

DESCRIPTION OF THE PREFERRED EMBODIMENTS

Figure 1:
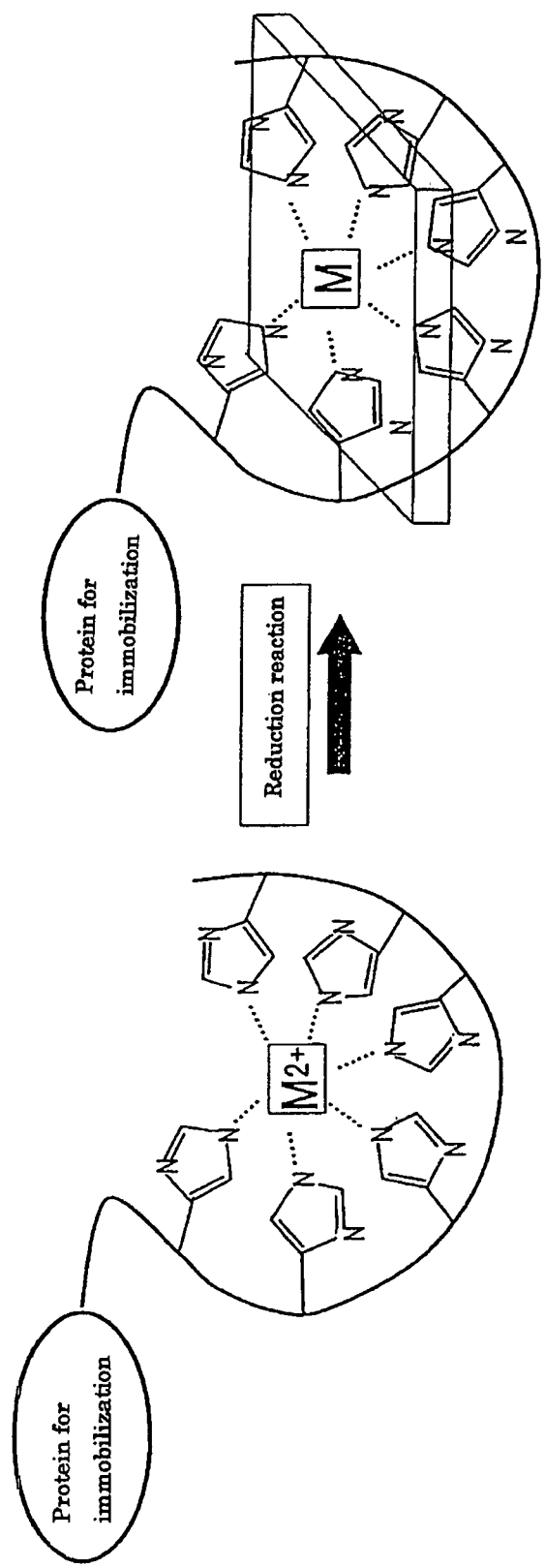
FIG. 1 is a scheme of a principle of the immobilization method.

Hereinafter, the present invention will be explained in detail.

<1> Biological Molecule-Immobilized Chip of the Present Invention

The biological molecule-immobilized chip of the present invention is a biological molecule-immobilized chip comprising: an electrically conductive support; and a biological molecule immobilized on the electrically conductive support via a metallic atom, in which the biological molecule has a portion capable of forming a coordination bond to a metal ion; and the metallic atom is generated by reduction of the metal ion. Examples of the biological molecule-immobilized chip include a protein chip on which a protein is immobilized and nucleic acid-immobilized chips such as a DNA chip on which a nucleic acid is immobilized.

Hereinafter, the protein chip will be explained.

A length of the protein having the portion capable of forming a coordination bond to a metal ion is not limited, and the protein may be a peptide.

A type of the portion capable of forming a coordination bond to a metal ion is not limited, and examples of the portion include a molecular chain and a molecular skeleton containing atoms such as a nitrogen atom, a sulfur atom and an oxygen atom, capable of forming a coordination bond to a metal. Such molecular chain or molecular skeleton may be a peptide or a compound other than peptide. Specifically, examples of the molecular chain and molecular skeleton capable of forming a coordination bond to a metal ion include a peptide containing polyhistidine (a polyhistidine tag), polyfilin, and a peptide or a compound containing thiol groups. Of those, the polyhistidine tag is particularly preferable. Here, the polyhistidine tag refers to a polypeptide containing two or more histidine residues. The number of histidine residues in the peptide is two or more, and is a number which does not adversely affect the function of the protein to be immobilized, but the number of histidine residues is preferably 6. The polyhistidine residues are not necessarily continuous in the peptide, and one or several amino acids other than histidine may be inserted between histidne residues in the peptide. The portion capable of forming a coordination bond to a metal ion such as the polyhistidine tag may be fused to any site of the protein to be immobilized, but is preferably fused to an amino-terminus or a carboxy-terminus of the protein.

The protein chip of the present invention is useful for, e.g., screening of a medicine that binds to a target protein; diagnosis using antibodies and the like; production of a useful substance by using an immobilized enzyme; purification of a protein; and analysis of a protein structure by means of SPM. Specific examples of a protein immobilized via the portion capable of forming a coordination bond to a metal ion in the protein chip of the present invention used for these objects include the proteins as described below. That is, the proteins include: protein hormones or peptide hormones such as insulin, adrenocorticotropic hormone (ACTH), and oxytocin; enzymes such as cholinesterase, amylase, and pepsin and precursors thereof; antibodies that recognize antigens such as HBs antigen and HIV antigen; and antibody-binding proteins such as protein A. Random proteins may also be used as a protein library. The immobilized proteins in the present invention may be non-natural proteins such as chemically synthesized proteins, and the immobilized proteins in the present invention also include peptides.

A metallic atom to be generated by reduction of a metal ion in the protein chip of the present invention is preferably a metallic atom which is generated by reduction of the metal ion capable of forming a coordination bond with a metal ion-binding portion of the protein. When the polyhistidine-fusion protein is used as a protein having a portion capable of forming a coordination bond to a metal ion, a metallic atom generated by reduction of a divalent cation such as $Cu^{2+}$, $Zn^{2+}$, $Ni^{2+}$, $Ca^{2+}$, $Co^{2+}$ or $Mg^{2+}$ is preferable. An electrically conductive support that constitutes the protein chip of the present invention means a support to which a electric potential can be applied. Examples of the electrically conductive support include: a support consisting of a metal; a support consisting of a semiconductor such as indium tin oxide (ITO), GaAs, or silicon; and a support consisting of carbon. Of those, the support consisting of a metal is preferable, and a support consisting of gold, silver, copper, aluminum, or platinum is particularly preferable.

The present invention also provides a protein chip in which a protein having a portion capable of forming a coordination bond to a metal ion is immobilized via a metallic atom to a pointed top of an electrically conductive support having the pointed top. Here, examples of the electrically conductive support having the pointed top include a support which itself has a pointed top, such as a platinum rod having a pointed top. Examples of such an electrically conductive support also include one in which a protein is immobilized to a pointed top of electrically conductive support obtained by attaching the electrically conductive support to a substrate such as silicon having a pointed top. Example of such an electrically conductive support include a probe of a cantilever to be used for a scanning probe microscope (SPM) (JP 05-026614 A), or an atom probe microscope (JP 05-018742 A), in which an electrically conductive support such as platinum is attached onto the substrate such as silicon. When proteins are immobilized on the pointed top of the electrically conductive support, the proteins can be immobilized at the rate of one or several molecules with respect to one electrically conductive support. In particular, such protein chip is useful as a sample for SPM and an atom probe microscope, and can be prepared by applying an electrical potential to the pointed top of the electrically conductive support. When electrical potential is applied to the pointed top of the electrically conductive support, single or several molecules of a protein can be immobilized because the potential is concentrated on the pointed top by an edge effect (Pure Appl. Chem. Vol. 72 No. 8, pp 1483-1492, (2000)).

The protein chip of the present invention includes a chip in which a protein having a portion capable of forming a coordinate bond to a metal ion is bound on an electrically conductive support via a metallic atom. However, a protein chip in which the electrically conductive support is carried on a substrate is preferable. Here, the term "the electrically conductive support is carried on a substrate" refers to a chip in which the electrically conductive support is bound sequentially on the overall surface of the substrate, or a chip in which plural of conductive supports are bound to the substrate so that the plural of conductive supports are arranged at constant intervals on the substrate. When plural proteins are immobilized on the protein chip of the present invention, all proteins are not necessarily immobilized on the electrically conductive support via the metallic atom, and at least a part of the proteins may be immobilized on the electrically conductive support via the metallic atom. In other words, a part of the proteins may be immobilized without the metallic atom, for example, some of the proteins may be bound via a metal ion.

Examples of a material that can be used as a substrate include plastic, an inorganic polymer, a natural polymer, and a ceramic. Specific examples of the plastic may include: polyethylene, polystyrene, polycarbonate, polypropylene, polyamide, a phenol resin, an epoxy resin, a polycarbodiimide resin, polyvinyl chloride, polyvinylidene fluoride, polyethylene fluoride, polyimide and an acrylic resin. Specific examples of the inorganic polymer include glass, crystal, carbon, silica gel and graphite. Specific examples of the natural polymer include cellulose, a cellulose derivative, chitin, chitosan, alginic acid and alginate. Specific examples of the ceramic include alumina, silica, silicon carbide, silicon nitride and boron carbide.

Examples of a shape of the substrate include a film, a flat plate, grain, a molded piece (a bead, a strip, a well or strip of a multi-well plate, a tube, a mesh, a continuous foaming form, a membrane, paper, a needle, fiber, a plate, a slide, and a cell culture dish), latex, and a probe of a cantilever. Size of the substrate is not particularly limited.

The above embodiments are explained for protein chips, however, the same kinds of a portion capable of forming a coordination bond to a metal ion, electrically conductive support, metallic atom, substrate and the like as described above may be employed for a chip on which other biological molecule is immobilized.

<2> Method of Manufacturing a Biological Molecule-Immobilized Chip

The biological molecule-immobilized chip of the present invention can be manufactured by a method comprising the steps of allowing a biological molecule having a portion capable of forming a coordination bond to a metal ion to form a coordination bond to a metal ion, bringing the resultant complex adjacent to an electrically conductive support and applying a reduction potential to the electrically conductive support to immobilize the biological molecule having the portion capable of forming a coordination bond to the metal ion on the electrically conductive support.

A manufacturing method of the protein chip is explained below.

A protein having a portion capable of forming a coordination bond to a metal ion immobilized on the protein chip of the present invention may be obtained by, for example, expressing a vector containing a DNA which encodes a fusion protein having a peptide capable of forming a coordination bond to a metal ion in vitro such as in a reticulocyte lysate, or in host cells such as $E.\ coli$ cells or insect cells, and purifying the expressed protein. Such a protein may also be obtained by means of chemical synthesis. A protein may be prepared separately and chemically bound to the portion capable of forming a coordination bond to metal ion. A protein containing the polyhistidine tag, which is a preferable protein in the present invention, may be produced by, for example, inserting a DNA which encodes a protein of interest into a known polyhistidine-fusion protein expression vector (for instance, pET series, manufactured by Novagen), expressing the fusion protein by transforming $E.\ coli$ or the like with the vector, and purifying the fusion protein by means of an affinity column or the like. Furthermore, such a protein may be obtained by synthesizing an oligonucleotide including a nucleotide sequence which encodes the polyhistidine tag and a complementary strand of the oligonucleotide, hybridizing the both strands, inserting the obtained DNA into an expression vector containing a DNA which encodes the protein of interest so as to express the fusion protein, expressing the fusion protein by transforming $E.\ coli$ or the like with the obtained vector, and purifying the expressed protein.

The protein having a portion capable of forming a coordination bond to a metal ion used for immobilization is not necessarily a purified protein in the present method, because the protein having the portion can be specifically immobilized on the protein chip. That is, a lysate, an extract and the like from $E.\ coli$ or a recticulocyte lysate which contains the protein may be used for immobilization directly. In this case, it has a benefit of omission of purification procedure.

In the manufacturing method of the present invention, the metal ion that forms the coordination bond with the protein having the portion capable of forming a coordination bond to the metal ion means a metal ion capable of forming a coordination bond with such portion of the protein. In the case where the polyhistidine-fusion protein is used as a protein having the metal ion-binding portion, a divalent cation such as $Cu^{2+}$, $Zn^{2+}$, $Ni^{2+}$, $Ca^{2+}$, $Co^{2+}$, or $Mg^{2+}$ is preferably used as a metal ion. The coordination bond between each of those metal ions and the protein having the portion capable of forming a coordination bond to the metal ion may be formed by adding a salt such as $NiCl_2$ corresponding to the metal ions in a buffer containing the protein. It is preferable to dialyze the coordinate bond complex of the metal ion and the protein in a metal ion-free buffer in order to remove a free metal ion after the reaction of coordination bond formation.

The term "bringing adjacent to the electrically conductive support" in the present manufacturing method, means to bring the coordinate bond complex between the metal ion and the protein having the portion capable of forming a coordination bond adjacent to the electrically conductive support, and preferably means immersing the electrically conductive support into a solution containing the coordinate bond complex. The solution in which the electrically conductive support is immersed is not particularly limited as long as an electric potential can be applied, and a phosphate buffer solution or the like may be used.

In the manufacturing method, application of an electric potential to the electrically conductive support may be carried out by: for example, immersing the electrically conductive support and a reference electrode in an electrolyte solution containing the coordinate bond complex of the metal ion and the protein; and applying the electric potential by using a normal electric power supply. Examples of the reference electrode include a silver-silver chloride electrode. The potential for application is a reduction potential which is a minus potential against the reference electrode. Preferable potential as the reduction potential differs depending on types of the electrically conductive supports, and when platinum is used as the electrically conductive support, the potential is preferably −10 mV or lower against the reference electrode, is more preferably −100 mV or lower against the reference electrode, and is particularly preferably −200 mV or lower against the reference electrode.

In manufacturing the protein chip in which the electrically conductive support is carried on the substrate, the electrically conductive support may be bound onto the substrate according to the conventional method, and examples of the method include sputtering, a vapor deposition method, an ion-plating method, an electroplating method, and a non-electroplating method.

The above embodiments are explained for methods of manufacturing protein chips, however, the same procedures as described above can be applied in manufacturing a chip in which other biological molecules are immobilized.

<3> Analysis Method of the Present Invention

The analysis method of the present invention is a method of analyzing a biological molecule or a binding molecule in a sample, comprising reacting the biological molecule immobilized on the biological molecule-immobilized chip of the present invention with the sample containing a molecule specifically binding to the biological molecule, and detecting the molecule bound indirectly to the chip via binding to the immobilized biological molecule.

Analysis method using the protein chip is explained below.

Examples of a sample containing a protein-binding molecule capable of specifically binding to the protein immobilized on the protein chip include samples which contain a protein (a peptide is included), an antigenic substance, a nucleic acid and a medical compound. Those protein-binding molecules may be one kind of molecule, or a mixture of random proteins as a protein library, furthermore, a mixture of random compounds may be used as a compound library. Each of the samples containing those protein-binding molecules may be a solution prepared by dissolving those molecules in an appropriate buffer solution or a biological sample such as blood or cell extracts.

The analysis method of the present invention may be used for various applications. When a medical target protein related to a specific disease is used as the immobilized protein and a library of medical compounds is used as protein-binding molecules, the method may be utilized for screening of medical compounds which bind to the target protein. In addition, when a sample such as blood that possibly contains an antigen is used as a sample containing a protein-binding molecule and the antibody specifically recognizing the antigen is used as the immobilized protein, the analysis method may be applied for diagnosis of diseases depending upon the presence or absence of antigens. In the case where a mixture of random proteins is immobilized and used as a protein library, and a specific protein or specific compound is used as a protein-binding molecule, the analysis method may be applied for functional analysis for searching a protein which specifically binds to the specific protein or the specific compound.

A measuring object may be the immobilized protein or the protein-binding molecule. The detection of the protein-binding molecule bound indirectly to the support via binding to the immobilized protein may be performed as described below. It is preferable to block the electrically conductive support by contacting it with an excessive amount of a bovine serum albumin (BSA), casein, a salmon sperm DNA or the like after immobilization of the protein, in order to prevent non-specifically binding of a protein-binding molecule to the electrically conductive support or the substrate during reaction.

After reaction of the immobilized protein and the sample containing the protein-binding molecule, the same procedure as a normal solid phase immunoassay may be performed to detect the protein-binding molecule bound to the immobilized protein. When the immobilized protein is a measuring object, for instance, the protein-binding molecule which has been labeled with a labeling substance is reacted with the protein chip, and then the labeling substance bound on the electrically conductive support is detected or quantified to thereby detect or quantify the protein-binding molecule, resulting in the detection or quantification of the immobilized protein.

When the protein-binding molecule is a measuring object, the protein-binding molecule labeled with a labeling substance is further added in the reaction system during the reaction of the protein chip and the protein-binding molecule, and the amount of the protein-binding molecule in the sample can be determined indirectly by measuring the amount of the labeling substance bound to the immobilized protein (an inhibition technique).

The protein-binding molecule bound to the immobilized protein may be detected by a reaction of the antibodies that are able to bind to the molecule specifically. For example, when the protein-binding molecule is antigen and the immobilized protein is antibody (primary antibody) against the antigen, the protein-binding molecule may be detected by reacting the other labeled antibody (secondary antibody) with the complex of the electrically conductive support-primary antibody-antigen to form the complex of the electrically conductive support-primary antibody-antigen-secondary antibody, and detecting based on amount of the secondary antibody in the complex (a sandwich technique).

The labeling substance may not always be a substance detectable for itself. For instance, when a biotin is used as a labeling substance, the protein-binding molecule may be detected indirectly by using an enzyme conjugated with avidin or streptoavidin which specifically binds to biotin.

The present invention provides an analysis method of an immobilized protein or a protein-binding molecule in a sample, comprising reacting the protein immobilized on the protein chip with a sample containing a protein-binding molecule capable of binding to the immobilized protein specifically, and dissociating a complex of the immobilized protein and the protein-binding molecule obtained by the reaction from the electrically conductive support by applying an oxidation potential to the electrically conductive support.

The protein can be dissociated from the electrically conductive support by applying the oxidation potential to the support on which the protein is immobilized. Specifically, the complex immobilized on the protein chip can be dissociated by immersing the protein chip used for the reaction with the protein-binding molecule into an electrolyte solution, and applying the oxidation potential to the electrically conductive support of the protein chip against a reference electrode. Here, the potential to be applied is a plus potential against the reference electrode. In the case where platinum is used as an electrically conductive support, the oxidation potential is preferably +10 mV or higher against the reference electrode, and is more preferably +100 mV or higher against the reference electrode. In the analysis method of the present invention, the complex dissociated from the electrically conductive support may be analyzed directly or may be analyzed after separating the protein-binding molecule from the immobilized protein. In addition, analysis of the immobilized protein or the protein-binding molecule in the sample also includes qualitative analyses such as various kinds of chromatographies and mass spectroscopy in addition to the above quantitative analyses in the analysis method of the present invention.

<4> Method of Purifying a Biological Molecule of the Present Invention

The present invention also provides a purification method of a biological molecule using the biological molecule-immobilized chip of the present invention. The biological molecule is preferably a protein. The purification method of a protein of the present invention includes the steps of immersing an electrically conductive support in a solution containing a metal ion and a protein having a portion capable of forming a coordination bond to the metal ion, applying a reduction potential to the electrically conductive support to immobilize the protein on the support, immersing the support obtained in the above step on which the protein is immobilized into a solution for dissociation, and applying an oxidation potential to the electrically conductive support to dissociate the protein from the support. In the purification method of the present invention, washing operation may be performed between the immobilization step and the dissociation step in order to decrease contamination of foreign proteins.

The same kinds of metal ion, protein, electrically conductive support and the like as those described above may be used for the purification method, and the same reaction conditions such as a potential to be applied as those described above may also be used. In addition, the solution for dissociation is not particularly limited so long as the potential can be applied. For instance, a phosphate buffer solution may be used, and purification can be performed either in batch-system or flow-system. The electrically conductive support used for purification may have any one of various shapes, but it preferably has such a shape that the surface area becomes large, for example, an electrically conductive support having a broom or sponge shape for enhancing the purification efficiency is preferable. According to the method of the present invention, there is no need to use a buffer solution for adsorption and elution of a protein used for normal purification, and the protein of interest can be purified without dilution.

<5> Immobilizing Method of the Present Invention

The present invention further provides an immobilizing method for a molecule including the steps of allowing a molecule having a portion capable of forming a coordination bond to a metal ion to form a coordination bond to the metal ion; bringing the resultant complex adjacent to the electrically conductive support; and applying a reduction potential to the electrically support to immobilize the molecule having the portion on the electrically conductive support. The molecule immobilized is not particularly limited, and may be a biological molecule such as a protein or a nucleic acid, or may be a non-biological molecule such as a low molecular weight polymer. The immobilizing method may be performed in the same way as "Method of manufacturing biological molecule-immobilized chip" as described above.

EXAMPLES

Hereinafter, the present invention is explained specifically by referring to the examples. However, the present invention is not limited to the examples.

(1) Construction of Expression Plasmid for Polyhistidine-Fused Protein A, and Expression of Polyhistidine-Fused Protein A in *E. coli* and Purification Thereof A protein for immobilization was prepared by linking polyhistidine to the string of 5 repeated B subunit of protein A (amino acid sequence: SEQ ID NO: 4). DNA encoding B subunit of the protein A was amplified by means of PCR. A mixture of a chemically synthesized polynucleotide (SEQ ID NO: 3) and its complementary strand polynucleotide (SEQ ID NO: 5) was used as a template. By employing a 5'-side primer having PstI and AccI sites (SEQ ID NO: 1) and a 3'-side primer having KpnI and AccI sites (SEQ ID No: 2) as primers, PCR was carried out for 30 cycles of 95° C. for 60 seconds, 60° C. for 30 seconds and 72° C. for 60 seconds.

The obtained PCR products were digested with AccI, and plural number of DNAs each encoding a B subunit of the protein A was ligated with each other by using a ligation kit (Takara Bio Inc.). The products encoding the protein A can be ligated in one direction by means of AccI, because the AccI recognition sequence is a non-palindromic sequence. The ligation products were subsequently subjected to agarose gel electrophoresis, and those having a length of 5 repeats of B subunits of the protein A were excised from the gel. Using a blunting kit (Takara Bio Inc.), the products were blunted and inserted into EcoRV sites of pBluescript II SK (STRATAGENE). The plasmids were used to transform *E. coli* and isolated from the obtained colonies, and the nucleotide sequence was determined with a nucleotide sequencer in accordance with a conventional method. The resultant plasmid was named as pBluescript II SK-proteinA.

A DNA encoding a polypeptide containing polyhistidine (amino-acid sequence: SEQ ID NO: 8) was connected to a carboxy-terminus of the DNA encoding protein A using the synthetic DNAs (SEQ ID NOS: 6 and 7) as follows. The synthetic DNAs of SEQ ID NOS: 6 and 7 were dissolved in 10 mM of Tris-EDTA buffer in the same test tube and heated at 64° C. for 1 minute. After heating, the solution was left for cooling to room temperature to thereby hybridize to form a double strand DNA. The DNA sequence corresponding to the polypeptide containing polyhistidine was inserted into pBluescript II SK-proteinA digested with Hind III and KpnI. The nucleotide sequence was confirmed in the same manner as that described above. The resultant plasmid was named as pBluescript II SK-proteinA-His.

The pBluescript II SK-proteinA-His plasmid was introduced into competent cells of *E. coli* M15 by electroporation and recombinant *E. coli* was obtained based on ampicillin-resistance. The expression of the protein was induced by culturing the resultant recombinant *E. coil* in an LB broth at 37° C., adding Isopropyl-Thio-β-D-Galactopyranoside to the LB broth at a final concentration of 0.1 mM when the absorbance at a wavelength of 600 nm (concentration of bacterial cells) became 0.8, and culturing the *E. coli* for additional 4 hours. A soluble fraction was obtained from the bacterial cells after ultrasonication and was loaded onto IgG-sepharose column (Pharmacia K.K.) to purify the expressed protein, and thereby polyhistidine-fused protein A was obtained.

(2) Electrochemical Immobilization of Polyhistidine-Fused Protein A

The polyhistidine-fused protein A obtained in the above section (1) was dissolved in 0.1 M of a sodium phosphate buffer solution (pH 5.8) at the final concentration of 0.3 mg/ml and $NiCl_2$ was further added at the final concentration of 200 mM. After reaction at 4° C. for 2 hours, the polyhistidine-fused protein A was allowed to form a coordination bond to $Ni^{2+}$ ion. In order to remove free $Ni^{2+}$ ion, 1 ml of solution containing the polyhistidine-fused protein A-$Ni^{2+}$ complex was poured into a dialysis cassette (Slide-A-Lyzer, Pierce Biotechnology, Inc) and dialyzed twice for each 20 minutes in 1,000 ml of an $Ni^{2+}$-free sodium phosphate buffer solution (pH 5.8). The coordination of $Ni^{2+}$ ion was confirmed with atomic absorption analysis by means of an atomic absorption spectrophotometer AA-670 (Shimazu Corporation).

A platinum microelectrode as a support for immobilization was immersed in the solution containing the $Ni^{2+}$ ion-bound polyhistidine-fused protein A. An electric potential was applied by using a three-electrode system including the platinum electrode as a working electrode, a platinum coil as a counter electrode, and a silver-silver chloride electrode as a reference electrode to thereby carry out an immobilization reaction. After application of an initial potential of +300 mV for 5 seconds, a constant potential of −100 mV was applied for 5 minutes. The platinum microelectrode was prepared by inserting a platinum wire having external diameter of 50 μm into a soda glass tube (1.2 mm in external diameter), encapsulating with a heater, and polishing its edge with a diamond paper (0.1 μm mesh).

Generally, when electric potential is applied, a non-faraday current based on an electric charge passes. However, in the case where reductive reaction occurs, non-faraday current as well as faraday current is observed. Change of a divalent nickel ion to a zerovalent nickel atom due to the application of the reduction potential can be confirmed by measuring the faraday current. The value of the faraday current was determined by a difference between a value of an actual current and a value of non-faraday current measured in a reaction system containing no $Ni^{2+}$ ion. Faraday current of 320 μA/cm$^2$ was observed, which confirmed that the divalent nickel ion has changed to the zerovalent nickel atom by the immobilization reaction.

(3) Evaluation of Immobilization State of Polyhistidine-Fused Protein A

Evaluation of the immobilization state of Ni-bound polyhistidine-fused protein A was carried out by utilizing specific binding between protein A and IgG antibody protein. The polyhistidine-fused protein A-immobilized microelectrode obtained in the above section (2) was immersed in 0.1 M sodium phosphate buffer solution (pH 7.0) containing 0.5 mg/ml of a horseradish peroxidase-conjugated IgG (Wako Pure Chemical Industries, Ltd.). After incubation at room temperature for 1 hour, the microelectrode was subjected to ultrasonic cleaning by means of an ultrasonic cleaner W-113 (Honda) in the 0.1 M sodium phosphate buffer solution (pH 7.0) containing no horseradish peroxidase-conjugated IgG. Subsequently, the microelectrode was immersed in peroxidase luminous substrate solution (Duolux, manufacturing by Pierce Biotechnology, Inc.). An amount of luminescence was measured with a luminometer Gene Light 55 (Microtec Co., Ltd), and a luminescence state was also observed by means of a high sensitivity CCD camera L-1100 (KEYENCE CORPORATION).

Figure 2:
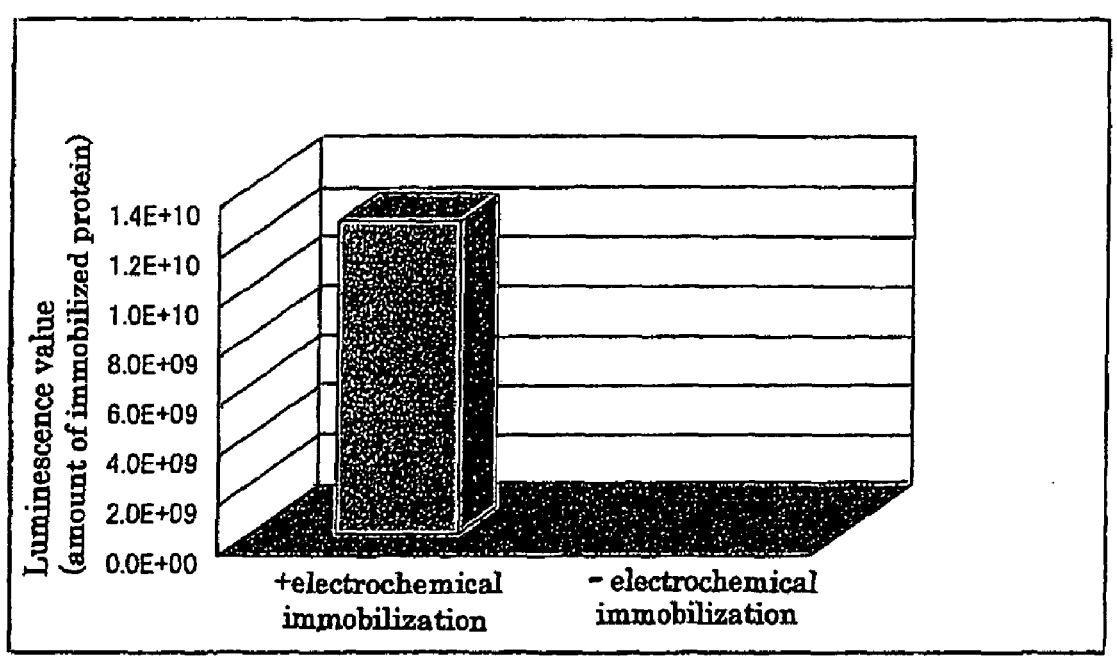
FIG. 2 is a graph showing luminescence values.

FIG. 2 shows the measurement of the amount of luminescence. No luminous reaction occurred when an electrode was not applied with the electrical potential and was only immersed in the solution containing the polyhistidine-fused protein A bound to $Ni^{2+}$ ion. On the other hand, a luminous reaction was detected when a microelectrode was immersed in the solution containing the polyhistidine-fused protein A bound to $Ni^{2+}$ ion, and a reduction potential of −100 mV was applied to the microelectrode. The amount of luminescence measured with a photoelectric multiplier was 1.4×10$^{10}$ cps (count per second). Although not shown in FIG. 2, in the case where a potential was applied in the same manner as described above to the solution containing the polyhistidine-fused protein A that was not bound to $Ni^{2+}$ ion, no luminous reaction was detected.

Figure 3:
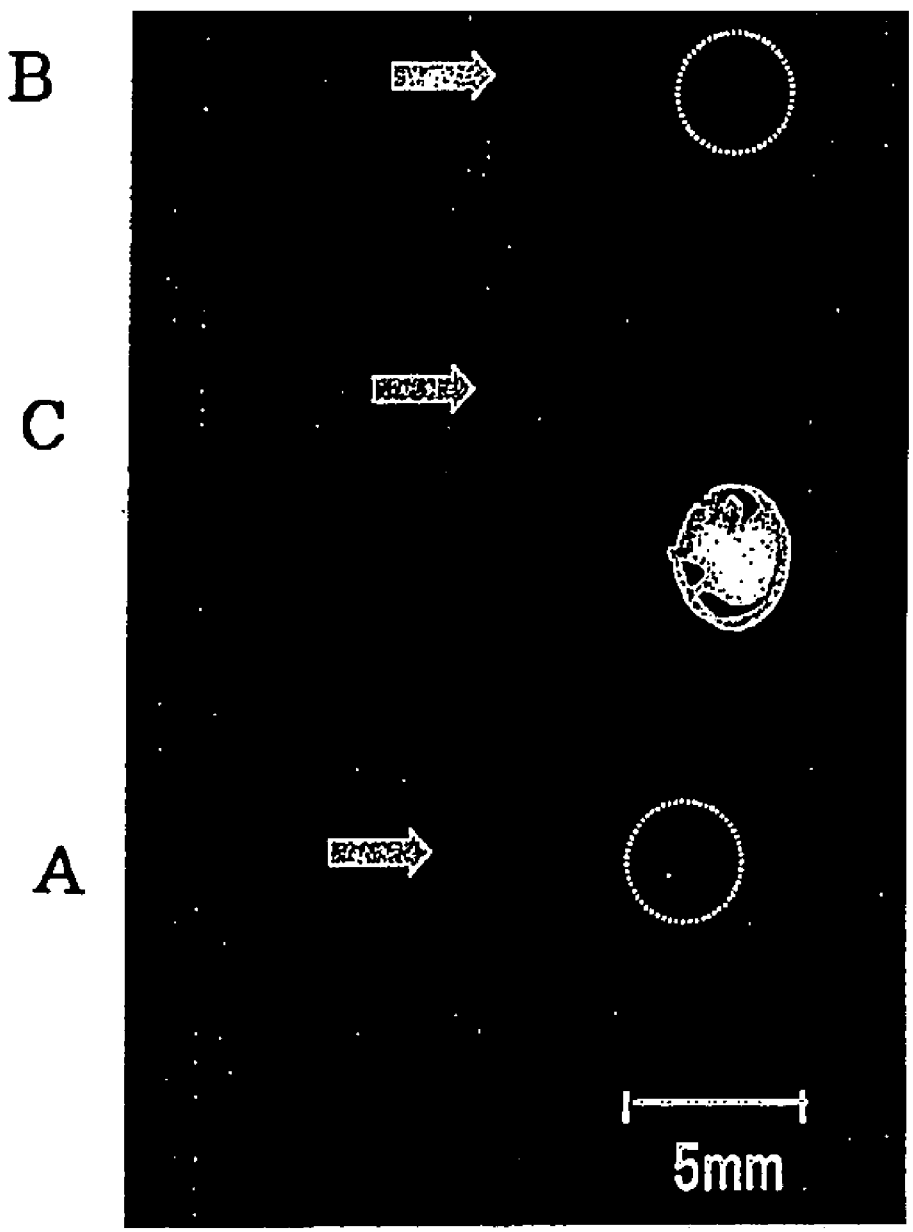
FIG. 3 is a luminescence image by CDD camera (photograph).

FIG. 3 shows a photographic image by a high sensitivity CCD camera of the electrode on which a luminous reaction was performed. No luminous reaction was detected when an electrode on which an electrochemical immobilization was performed by using the solution containing polyhistidine-fused protein A that was not bound to $Ni^{2+}$ ion (A). In addition, no luminous reaction was detected when an electrode was not applied with the potential and was only immersed to the solution containing the polyhistidine-fused protein A coordinately bound to $Ni^{2+}$ ion (B). On the other hand, a luminous reaction was detected when a microelectrode was immersed in the solution containing the polyhistidine-fused protein A coordinately bound to $Ni^{2+}$ ion, and a reduction potential of −100 mV was applied to the rnicroelectrode (C). Dotted lines show the location of the electrodes in (A) and (B) of FIG. 3, because the luminescence was not observed. As described above, it was confirmed that the polyhistidine-fused protein A was immobilized stably by reducing $Ni^{2+}$ ion coordinately bound to the polyhistidine-fused protein A to Ni atom.

Furthermore, in order to determine the ranges of the potential required for immobilization, immobilization was performed by applying the potential in the range of approximately +200 mV to −400 mV, and the resultant immobilized electrodes was evaluated for luminance using the horseradish peroxidase-conjugated IgG The result confirmed that the immobilization can be achieved as long as the potential is −100 mV or higher (data not shown).

(4) Dissociation of Immobilized Polyhistidine-Fused Protein A

The polyhistidine-fused protein A immobilized by the procedure as described above was dissociated from the platinum electrode by applying a potential of 250 mV. Dissociation of polyhistidine-fused protein A from the electrode was confirmed by the luminescence method using a horseradish peroxidase-conjugated IgG (data not shown). The range of the potential capable of dissociation was determined and it was found that dissociation can be achieved by applying a potential of +100 mV or higher.

(5) Immobilization of Polyhistidine-Fused Protein A on Platinum Support Having a Pointed Top A cantilever having a probe which is consisted of a silicon substrate and whose pointed top is coated with platinum (Micro Cantilever with platinum coat, manufacturing by Olympus Corporation) was used as an electrode. The polyhistidine-fused protein A was immobilized by the following procedure. That is, the cantilever was soaked into 5% of bovine serum albumin solution for blocking. The cantilever was immersed into the solution containing polyhistidine-fused protein A coordinately bound to Ni$^{2+}$ ion, and potential of −50 mV was applied for 5 minutes against the silver-silver chloride reference electrode in the same way as described above. Immobilization was confirmed by using an electron microscope.

(6) Purification of Polyhistidine Fusion Protein A From *E. coli* Lysate

Figure 4:
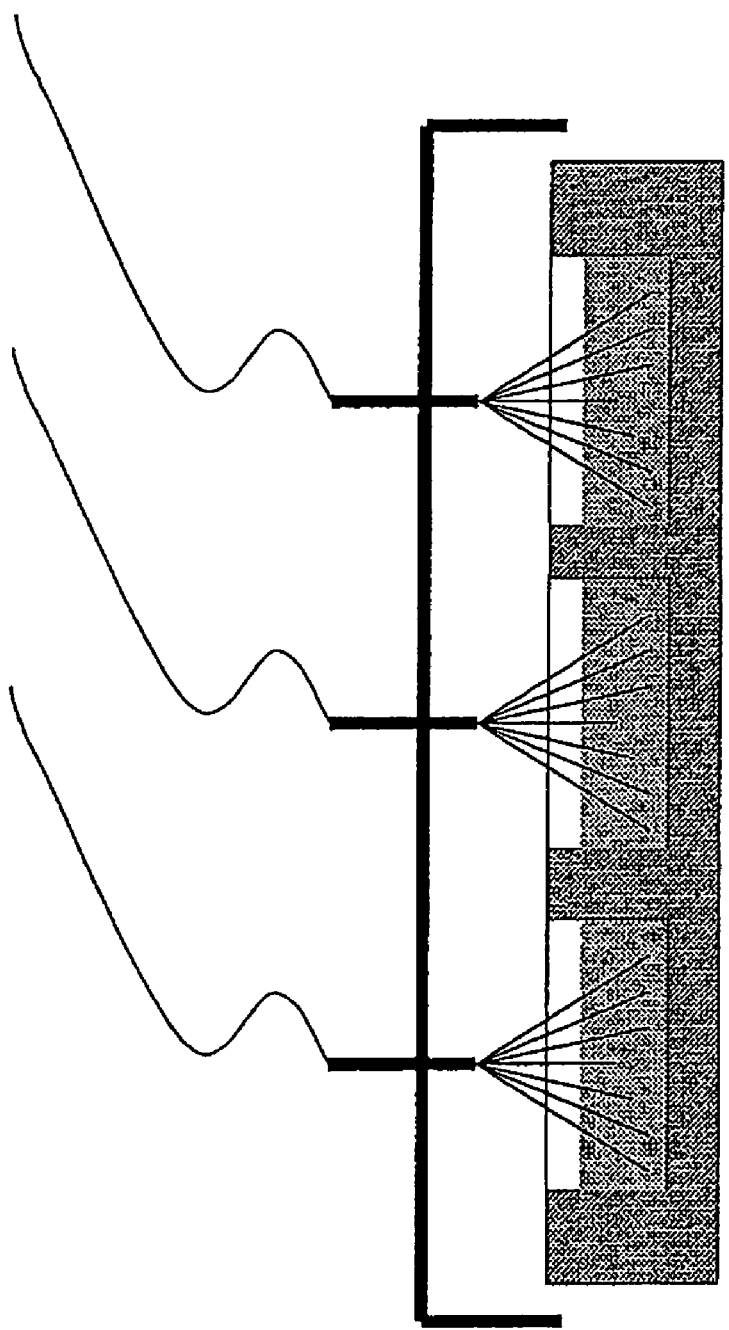
FIG. 4 is scheme of purification of a polyhistidine-fused protein A from *E. coli* lysate.

The *E. coli* transformed with the pBluscript II SK-protein A as described above was incubated in the 15 ml/well of LB broth in a six-well plate at 37° C. for 4 hours, and then IPTG was added to the broth and the transformant was further incubated for 4 hours. After completion of the incubation, the bacterial cells were precipitated by a plate centrifugator, and then the supernatant of the LB broth was replaced by the phosphate buffer solution containing Ni$^{2+}$ ion (the composition was the same as described above). Subsequently, the bacterial cells were disrupted by means of a probe-type ultrasonicater in each well of the plate, and then bloom-shape supports for purification were immersed in the solution as shown in FIG. 4. The polyhistidine-fused protein A in the solution was immobilized on the supports by applying a potential of −100 mV to the supports.

Then, the bloom-shape supports for purification were taken out from the solution, and immersed in buffer solution (0.1 M of KH$_2$PO$_4$—K$_2$HPO$_4$ and 0.1 M of KCl (pH 7.0)) for dissociation prepared in a different six-well plate. Then, potential of +250 mV was applied to the supports, and thereby, the immobilized polyhistidine-fused protein A was dissociated in the buffer solution for dissociation. As a result, 0.45 mg of the polyhistidine-fused protein A per well was purified. In conclusion, purification of a protein was attained rapidly and easily without dilution by elution buffer on a column or the like.

INDUSTRIAL APPLICABILITY

The biological molecule-immobilized chip of the present invention is preferably used for screening of a medicine and the like, because a biological molecule such as a protein can be immobilized stably in a constant orientation. In addition, the biological molecule-immobilized chip is preferably used for research purpose, because it allows the biological molecule to dissociate from the electrically conductive support, which makes it possible to reuse the substrate and biological molecule and to analyze the biological molecule after the reaction. Furthermore, it is useful for rapid and easy purification of the biological molecule.

What is claimed is:

1. A biological molecule-immobilized chip, wherein said chip comprises an electrically conductive support and a complex of a biological molecule and a non-ionic metallic atom immobilized directly on the electrically conductive support, wherein a portion of the biological molecule is bonded to the non-ionic metallic atom and said complex is bound to the support via the non-ionic metallic atom.

2. The biological molecule-immobilized chip according to claim 1, wherein said electrically conductive support has a pointed top, and said biological molecule is immobilized on the pointed top of the electrically conductive support via the non-ionic metallic atom.

3. The biological molecule-immobilized chip according to claim 1, wherein said electrically conductive support is carried on a substrate.

4. The biological molecule-immobilized chip according to claim 1, wherein said portion of the biological molecule which is bonded to the non-ionic metallic atom is polyhistidine.

5. The biological molecule-immobilized chip according to claim 1, wherein said electrically conductive support is a metal.

6. The biological molecule-immobilized chip according to claim 1, wherein said electrically conductive support is one or more metals selected from the group consisting of gold, silver, copper, aluminum, and platinum.

7. The biological molecule-immobilized chip according to claim 1, wherein said non-ionic metallic atom is generated by reduction of a divalent metal ion.

8. The biological molecule-immobilized chip according to claim 1, wherein said biological molecule is a protein.

9. A method of analyzing a biological molecule or a molecule in a sample, comprising:
   reacting a biological molecule immobilized on the biological molecule-immobilized chip according to claim 1 with a sample containing a molecule capable of specifically binding to the biological molecule;
   detecting a molecule bound indirectly to the chip via binding to the immobilized biological molecule, and
   analyzing the biological molecule immobilized on the biological molecule-immobilized chip or the molecule in the sample.

10. A method of analyzing a biological molecule or a molecule in a sample, comprising:
    reacting the biological molecule immobilized on the chip according to claim 1 with a sample containing a molecule capable of specifically binding to the immobilized biological molecule; and
    dissociating a complex containing the immobilized biological molecule and the molecule specifically binding to the biological molecule obtained from the reaction, from the electrically conductive support of the chip by applying an oxidation potential to the electrically conductive support.

* * * * *